(12) United States Patent
Capper et al.

(10) Patent No.: US 6,605,118 B2
(45) Date of Patent: *Aug. 12, 2003

(54) PROSTHETIC ATTACHMENT LOCKING ASSEMBLY HAVING PROSTHETIC ATTACHMENT LOCK

(75) Inventors: James W. Capper, Mt. Sterling, OH (US); Robert E. Arbogast, Mt. Sterling, OH (US); Jeffrey L. Doddroe, Washington C. H., OH (US); James M. Colvin, Hilliard, OH (US)

(73) Assignee: Ohio Willow Wood Company, Mount Sterling, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/769,399

(22) Filed: Jan. 26, 2001

(65) Prior Publication Data

US 2001/0001837 A1 May 24, 2001

Related U.S. Application Data

(62) Division of application No. 09/357,855, filed on Jul. 21, 1999, now Pat. No. 6,267,787.

(51) Int. Cl.7 .................................................. A61F 2/80
(52) U.S. Cl. .......................................... 623/36; 623/34
(58) Field of Search ............................... 623/36, 33, 34, 623/27, 32, 35, 38; 403/105, 152, DIG. 4

(56) References Cited

U.S. PATENT DOCUMENTS

| 980,457 A | * | 1/1911 | Toles |  |
| 5,163,965 A | * | 11/1992 | Rasmusson et al. | 623/36 |
| 5,226,918 A |  | 7/1993 | Silagy et al. | 623/32 |
| 5,702,489 A |  | 12/1997 | Slemker | 623/34 |
| 5,728,170 A | * | 3/1998 | Becker et al. | 623/37 |
| 5,888,234 A | * | 3/1999 | Littig | 623/38 |
| 6,267,787 B1 | * | 7/2001 | Capper et al. | 623/36 |
| 6,287,345 B1 | * | 9/2001 | Slemker et al. | 623/34 |
| 6,334,876 B1 | * | 1/2002 | Perkins | 623/34 |

* cited by examiner

Primary Examiner—Bruce Snow
(74) Attorney, Agent, or Firm—Oblon, Spivak, McClelland, Maier & Neustadt, P.C.

(57) ABSTRACT

A prosthetic attachment locking assembly includes a distal adaptor fittable in the bottom of a socket for a residual limb stump and has an upper surface configured to accept an end of a stump liner. The internal surface of the socket merges smoothly with the upper surface of the distal adaptor. The distal adaptor has a pin bore through which a lock pin of the stump liner may extend, and a lower surface having a plurality of projections. A lock body of a prosthetic attachment lock has a pinion gear engagable with the lock pin to lock the lock pin, and an upper surface matably engagable with the projections such that the lock body and the distal adaptor may be connected via the projections and the upper surface of the lock body. The pinion gear is mounted to a centering axle. A one-way clutch for the pinion gear incorporates a sleeve non-rotatably mounting the centering axle such that the centering axle does not bind when it is pressed to move longitudinally. The centering axle is thus movable against a biasing force of a spring to disengage the gear from the lock pin.

3 Claims, 3 Drawing Sheets

PROSTHETIC ATTACHMENT LOCKING ASSEMBLY HAVING PROSTHETIC ATTACHMENT LOCK

This application is a Division of application Ser. No. 09/357,855 filed on Jul. 21, 1999, now U.S. Pat. No. 6,267,787.

BACKGROUND OF THE INVENTION

1. Field of the Invention

The present invention is directed to a prosthetic attachment locking assembly which locks a residual limb stump to a prosthetic limb. More particularly, it relates to a prosthetic attachment lock incorporated into such an assembly.

2. Description of the Related Art

A prosthetic limb is conventionally secured to an amputee's residual limb stump by securing the prosthetic limb within a rigid socket part. This may commonly be done by shaping the socket such that it can form an air tight seal with the stump. In this case, a one way valve may be provided in the socket to permit air to be expelled from the socket as the stump is introduced, and the socket is held onto the stump by the resulting suction. While this is a comfortable form of suspension, an air leak due to stump shrinkage for example, can cause loss of suspension.

It is also known to secure the prosthetic limb to the stump by a lock pin. In this technique, the amputee first dons a sock-like sock liner formed of an elastomer with an optional fabric cover. The bottom end of the liner is formed of a rigid material such as urethane, and the lock pin extends from this rigid bottom. Such stump liners are well known, such as that manufactured and sold by The Ohio Willow Wood Company under the name Alpha Locking Liner. The pin is extended through the wall of the socket and a distal adapter mounted within or outside of the socket, and can be locked onto a prosthetic attachment lock mounted to the prosthetic limb to secure the prosthesis, optionally in conjunction with a suspension sleeve. Examples of a conventional locking assembly of this type are found in U.S. Pat. Nos. 5,507,837 and 5,888,234.

While conventional prosthetic attachment locking assemblies generally work well, they have a number of shortcomings. Amongst these is a tendency for the end of the lock pin to catch on a seam between the interior surface of the socket and the lip formed at the edge of the distal adapter when a distal adapter is fitted within the bottom of the socket. Another shortcoming is that the prosthetic attachment lock may also need to mate with the distal adapter through the intermediary of the bottom wall of the socket, which reduces the stability and structural rigidity of the joint. It is also necessary to use different distal adapters for test sockets which are made of a thermoplastic material, and definitive sockets which are made of a fiber reinforced laminate, and so it is necessary to use two kits for each prosthesis, which increases the final cost.

A further shortcoming of the conventional prosthetic attachment locks lies in the manner of releasing the lock pin from the locking device. Conventionally, the pin has a longitudinal series of rack-like serrations and extends through a pin bore of the lock body. The teeth of a pinion gear in the lock body extend into the pin bore to engage the teeth of the lock pin therein. The pinion gear is mounted for one way rotation to permit entry of the lock pin into the pin bore but lock the lock pin against removal. The lock pin can be released only by moving the pinion gear in a direction parallel to its rotational axis until it disengages from the lock pin, e.g., via a manual release button.

A problem with this conventional design is that the one way clutch incorporates the shaft onto which the pinion gear is mounted. Therefore, the force from the lock pin which has been tightened onto the gear is directly transferred to the gear shaft, which causes the shaft to bind and makes it difficult to manually push the manual release button sufficiently to release the lock pin.

SUMMARY OF THE INVENTION

It is therefore an object of the invention to overcome the aforementioned shortcomings of the conventional design.

It is a further object of the invention to provide a prosthetic attachment lock in which the pinion gear is more easily released from the lock pin while a load is being applied to the gear via the lock pin.

It is a further object of the invention to provide a more stable and rigid joint for the prosthetic attachment locking assembly.

It is a further object of the invention to provide a single prosthetic attachment lock which can be used with either a thermoplastic or thermoset socket and which can be reused.

It is a further object of the invention to provide a prosthetic leg with a better fit, better suspension and less noise by combining the reliability of a pin suspension with the comfort and performance of a suction suspension.

According to a feature of the invention, the above and other objects are achieved by a prosthetic attachment lock comprising a lock body having a pin bore into which a lock pin may be inserted, and a locking device in the lock body. The locking device includes a centering axle rotatably mounted in the lock body, a pinion gear mounted to the centering axle, a sleeve non-rotatably mounting the centering axle for longitudinal movement, and a one way clutch connected between the lock body and the sleeve.

A spring is engaged to bias the centering axle relative to the sleeve along the longitudinal axis of the centering axle such that the pinion gear engages the lock pin to lock the lock pin. The centering axle is movable against the biasing force of the spring to disengage the gear from the lock pin.

According to another feature of the invention, the above and other objects are achieved by a prosthetic attachment lock including a lock body having a pin bore into which a lock pin may be inserted, and a locking device in the lock body and having a gear engagable with the lock pin to lock the lock pin in the pin bore, disengaging means for permitting the gear to disengage from the lock pin, and means independent of the disengaging means for permitting only one way rotation of the gear.

According to yet another feature of the invention, the above and other objects are achieved by a prosthetic attachment locking assembly comprising a distal adaptor fittable in the bottom of a socket for a residual limb stump and having an upper surface configured to accept an end of a stump liner, the distal adaptor having a pin bore through which a lock pin of the stump liner may extend, and a lower surface having a plurality of projections. A lock body has an element engagable with the lock pin to lock the lock pin and an upper surface matably engagable with the projections such that the lock body and the distal adaptor may be connected via the projections and the upper surface of the lock body.

According to yet another feature of the invention, the above and other objects are achieved by a prosthetic attachment locking assembly comprising a rigid socket into which a residual stump having a stump liner with a lock pin may be introduced, and a distal adaptor fittable in the bottom of the socket and having an upper surface configured to accept the end of a stump liner. The internal surface of the socket merges smoothly with the upper surface of the distal adaptor.

According to yet another feature of the invention, the above and other objects are achieved by a prosthetic attachment locking assembly comprising a rigid socket into which a residual stump having a stump liner with a lock pin may be introduced, a prosthetic attachment lock, a distal adaptor fittable in the bottom of the socket and having an upper surface configured to accept the end of a stump liner and a lower surface having a plurality of projections extending through the wall of the rigid socket such that the distal adaptor may be fixed to the prosthetic attachment lock via the projections.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENT

Figure 1:
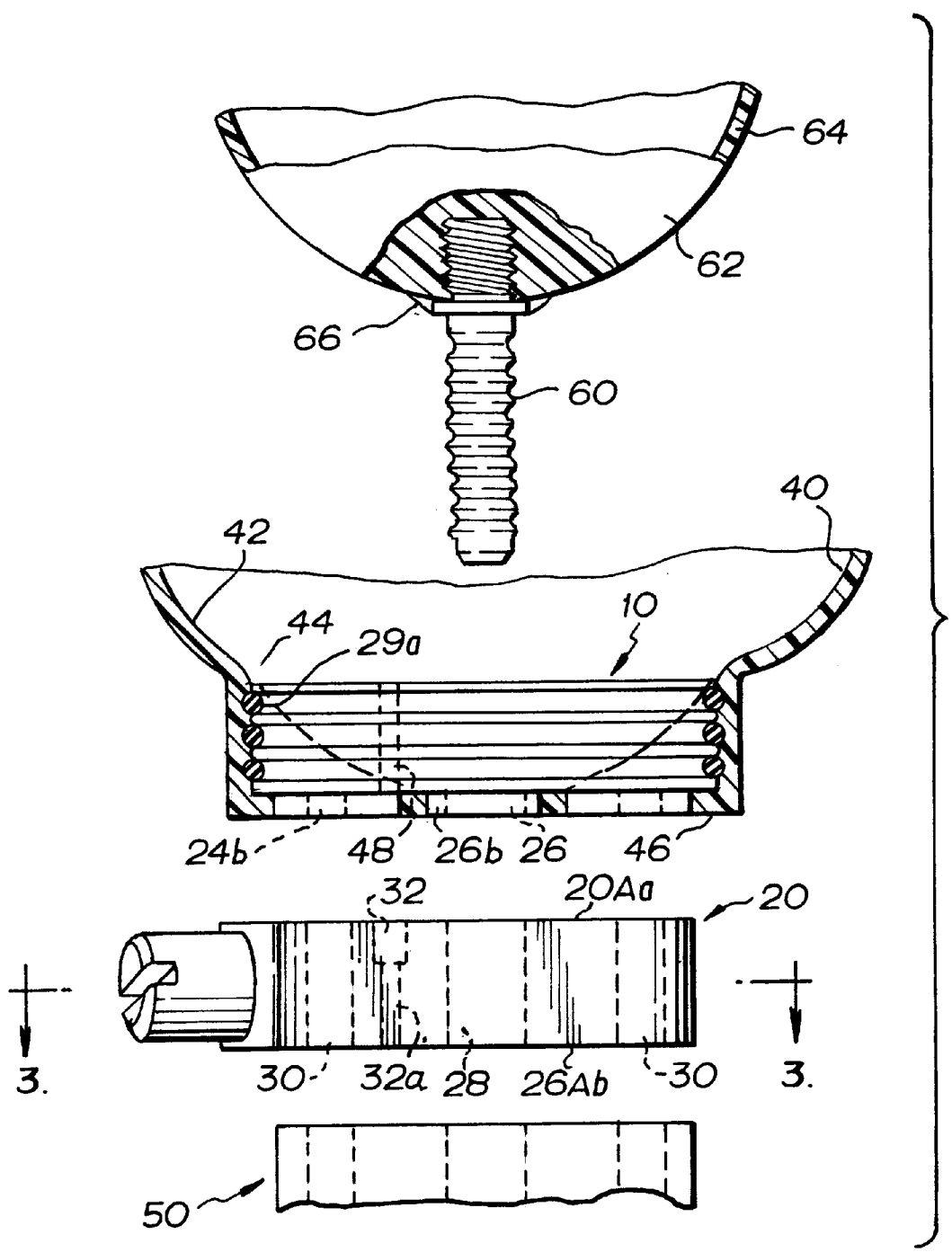
FIG. 1 is an exploded view of a prosthetic attachment locking assembly according to the invention.

A preferred embodiment according to the invention is illustrated with reference to the attached non-limiting figures in which the same reference numerals are used to refer to the same or similar parts throughout the various views.

Figure 2A:
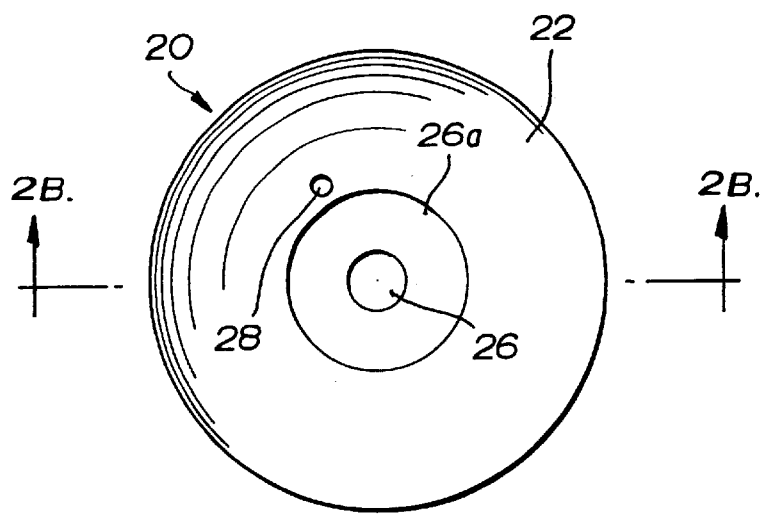
FIGS. 2A, 2B and 2C are respectively top, sectional and bottom views of a distal adapter according to the invention, in which the sectional view of FIG. 2B is taken along line B—B of FIG. 2A.
Figure 2B:
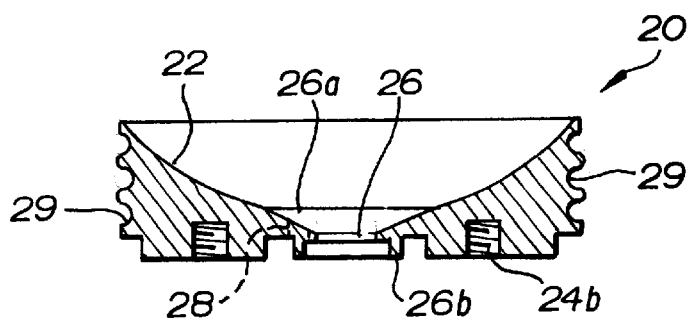
Figure 2C:
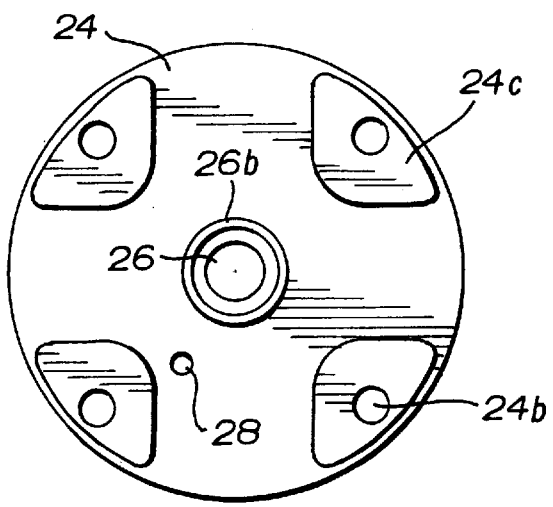

Referring first to FIG. 1, a prosthetic attachment locking assembly is composed of a distal adapter 10 and a prosthetic attachment lock 20. The distal adapter 10, shown in greater detail in FIGS. 2A–2C, is preferably formed of machined aluminum although other rigid materials having the requisite characteristics may be used. It is generally formed as a roughly cylindrically body having a part-spherical concave upper surface 22 and a generally planar lower surface 24. A central pin bore 26 extends through the body of the distal adapter 10 from the upper surface 22 to the lower surface 24. The upper part of the pin bore 26 is in the form of a conical outward taper 26a which merges with the upper surface 22, while the lower end of the pin bore 26 is extended downwardly by an annular rim 26b.

A number (four in this embodiment) of projections 24a extend integrally downward from the bottom surface 24, adjacent the periphery of the bottom surface and by the same distance as the rim 26b. The projections 24a form flat bottom surfaces into which threaded screw holes 24b are bored.

An air expulsion hole 27 extends through the body of the distal adapter from the top surface 22 to the bottom surface 24.

A series of annular grooves 29 in the peripheral cylindrical surface of the distal adapter can hold sealing rings such as O-rings 29a, for the purpose described below.

In the state illustrated in the figures, the distal adapter 10 is sealingly fitted into the bottom of a rigid socket 40. The sealing at the periphery of the distal adaptor 10 is assured by the sealing rings 29a. The socket may generally be of a conventional design except as noted below, and may be formed of a thermoplastic material or a carbon fiber laminate, although it may instead be formed of other materials which can satisfy the functional requirements of a prosthetic socket. Generally speaking, the socket 40 has an internal surface 42 whose shape can cooperate with a residual limb stump so that the stump can comfortably fit within the socket and form an air tight seal.

The distal adapter 10 may be fitted within the bottom of the socket 40 in a variety of ways, including press fitting the distal adaptor into the already formed socket, or by the socket being molded or laid up (laminated) around the distal adapter 10. In any case, the internal configuration of the inner surface 42 of the socket wall should be such that it forms a smooth or seamless transition to the edge of the top surface 22 of the distal adapter so that the end of the lock pin 60 of the prosthetic attachment locking assembly will not catch on a lip, and can smoothly be guided to the top surface 22 and the pin bore 26. This seamless merging can be accomplished by providing that the inner surface 42 of the wall of the socket, in its portion 44 located at and immediately above the edge of the top wall 22 of the distal adapter 10, has substantially the same radius and center as the part-spherical top surface 22. The radius of the top surface 22 is preferably 0.3 to 5 inches, more preferably 1.5 to 2 inches, and the outside diameter of the distal adapter 10 is preferably 1 to 3 inches.

As best seen in FIG. 1, the rim 26b and the projections 24a extend through the wall 20 of the bottom of the socket 40 and provide flat external surfaces coplanar with the bottom exterior surface 46 of this bottom wall. The projections 24a therefore provide surfaces integral with the distal adapter for secure and stable attachment of the prosthetic attachment lock 20, and the rim 26b provides a seal against air leakage from the joint between the air expulsion hole 27 and a colinear air hole 48 in the bottom of the socket 40.

The prosthetic attachment lock 20 has a lock body 20A which may be in the form of a flat disk with a generally rectangular shape (although in the illustrated embodiment the lock body is not precisely rectangular). It may be made of machined aluminum or another rigid material which is adaptable to the same purpose. The lock body 20A may have planar upper and lower surfaces 20Aa and 20Ab, and a pin bore 28 extending therethrough from the upper surface 20Aa to the lower surface 20Ab. Through holes 30 are also provided at positions which may be aligned with the threaded screw holes 24b in the projections 24a of the distal adapter 10. It is therefore possible to securely fix the lock body 20A to the distal adapter by screws or bolts which can pass through the holes 30 and be threaded into the screw holes 24b, thereby clamping the lock body 20A between the prosthetic limb 50 and the socket 40 and securely joining the socket 40 to the prosthetic limb.

The lock body 20A also has an air valve hole 32 which can hold a one way air valve 32c, e.g., an elastomeric "duck bill," and which has outlet 32a or 32b. The air valve hole is a aligned with, and communicates with, the air expulsion holes 27 and 48 for expelling to the outside the air which is displaced by the insertion of the residual stump into the socket. The one way valve 32c closes to maintain the suction once the stump is inserted.

Although the one way valve 32c is shown in its preferred location in the prosthetic attachment lock 20, it can be located in another part of the prosthetic attachment lock. Also, a muffler 32d made of micro-cellular foam or another suitable material may be provided at one of the outlets 32a or 32b. A filter (not shown) may be positioned at the valve so as to keep contaminants from the socket from reaching the valve.

Although the one way valve 32c is shown in its preferred location in the prosthetic attachment lock 20, it can be located in another part of the prosthetic attachment lock. Also, a muffler (not shown) made of micro-cellular foam or another suitable material may be provided at one of the outlets 32a or 32b. A filter (not shown) may be positioned at the valve so as to keep contaminants from the socket from reaching the valve.

The lock pin 60 may be mounted, e.g., by molding or screwing, to a rigid urethane body 62 secured or formed at the lower end of the stump liner 64. The body 62 has a dome-like lower surface which can mate with the upper surface 22 of the distal adapter 10. The lock pin has a series of tooth-like serrations and may be conventional, except that it further includes an annular sealing element 66 formed of rubber or some other elastomeric material and shaped to form an air tight seal with the conical taper 26a of the distal adapter when the lock pin 60 is locked into the prosthetic attachment lock.

Figure 3A:
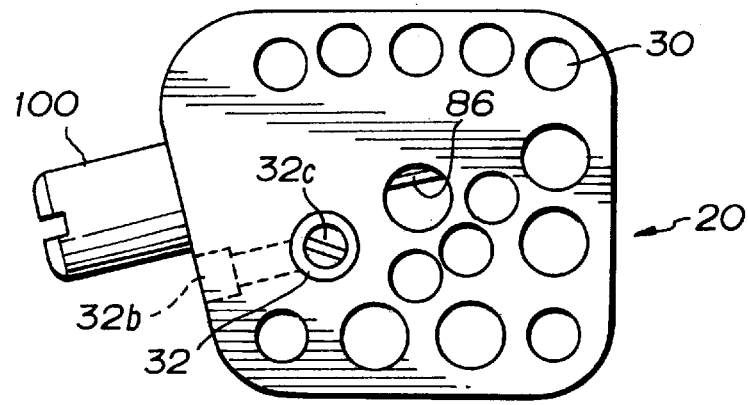
FIGS. 3A and 3B are respectively top and sectional views of a prosthetic attachment lock according to the invention, in which the sectional view of FIG. 3B is taken along line III—III of FIG. 1.
Figure 3B:
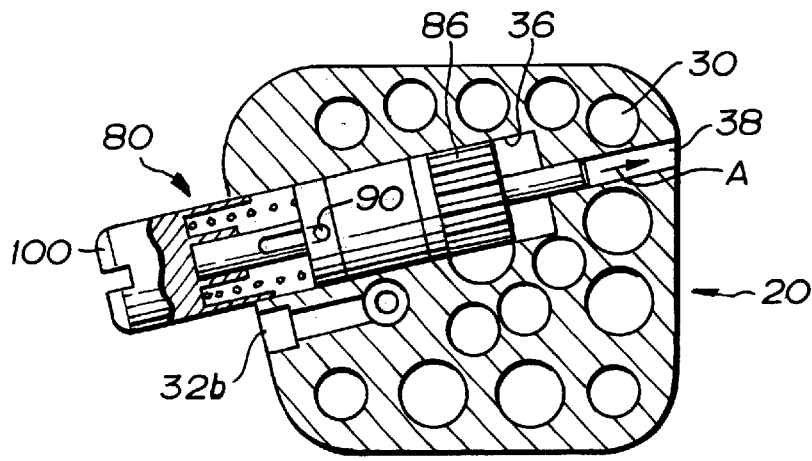
Figure 4:
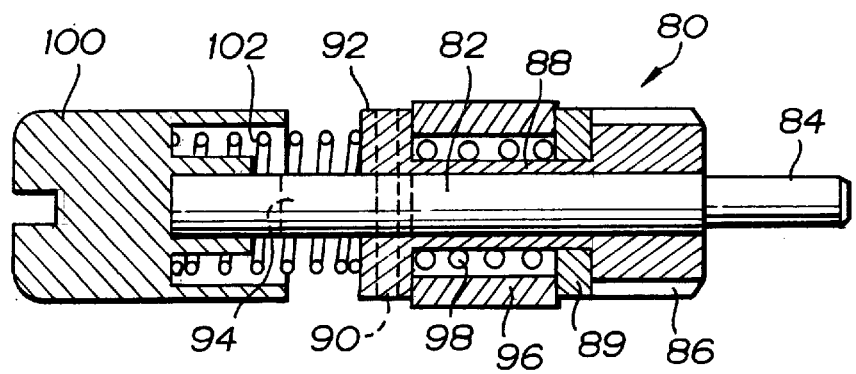
FIG. 4 is a detail showing a locking device according to the invention.

Referring particularly to FIGS. 3B and 4, a cylindrical bore 36 for housing the locking device is formed in the lock body 20A and extends from one of the side surfaces into the lock body such that it intersects the pin bore 28. It is extended by a smaller diameter centering the hole 38 which cooperates with the locking device as set forth below.

The locking device 80, which is best seen in FIG. 4, has a centering axle 82 which is extended by a pin 84 which is guided for longitudinal and rotational motion by the centering bore 38 of the lock body 20A acting as a bearing for the pin 84. A locking gear 86 is fixedly mounted on the centering axle and can be located within the bore 36 such that its teeth extend into the pin bore 28 and mesh with the serrations of the lock pin 60 when the lock pin 60 extends into the pin bore 28. As a result, movement of the lock pin 60 into the pin bore 28 will cause rotation of the locking gear 86 and the centering axle 82, but removal of the lock pin 60 is prevented by the one-way clutch (described below) which prevents opposite rotation of the locking gear 86. The above described locking device is conventional, except for the features of the one-way clutch set forth below.

The centering axle 82 is slidably mounted for movement along its length within the bore of a load bearing sleeve 88, which bore forms a linear bearing for the centering axle 82. However, rotation between the centering axle 82 and the sleeve 88 is prevented by a dowel 90 which extends through a bore in a flange 92 of the sleeve 88, and also extends through an elongated slot 94 of the centering axle 82.

The load bearing sleeve 88 cooperates with an outer sleeve 96 and clutch elements 98 of a one-way rotation clutch. A conventional clutch usable for this purpose may be the Stock Drive Products roller clutch model S99NH3MURC1012. The outer sleeve 96 of the clutch may be fixed by press fitting within the bore 36. On the other hand, the load bearing sleeve 88 is permitted by the one-way clutch to rotate in one direction within the bore 36. In turn, 5 the centering axle 82 and the locking gear 86 rotate with the sleeve 88 due to the dowel 90 extending through the slot 94. The length of the slot 94 is such as to permit the centering axle to move longitudinally within the sleeve 88 until the gear 86 disengages from a lock pin 60 in the pin bore 28.

A push button 100 is attached to an end of the centering axle and extends out of the lock body 20A. A spring 102 engaged between the push button 100 and the flange 92 of the sleeve 88 biases the locking gear 86 into the position shown in FIG. 3B in which it extends into the pin bore 28 so as to be able to engage and lock the lock pin 60 held therein. One can manually rotate the gear 86 by turning the push button 100. One can also manually inwardly push on the push button, against the biasing force of the spring, for causing the centering axle and the locking gear 86 to slide in the direction of the arrow A in FIG. 3B until the locking gear 86 exits from the pin bore 28. The locking gear 86 then disengages from the lock pin 60 which can be removed from the lock body 20A without impediment.

In this embodiment, the linear bearing support of the centering axle 82 within the bore of the sleeve 88 comprises an example of disengaging means for permitting the gear to disengage from said lock pin. The one-way clutch 96–98 held in place by sleeve 88 and retaining ring 89 comprises an example of means for permitting only one way rotation of the gear 86. This one-way clutch is independent of the disengaging means since clutch elements do not engage with the centering axle 82 or the inner bore of the sleeve 88.

During socket fabrication, the distal adapter is typically attached to a model of the user's stump. For a thermoplastic socket, the thermoplastic is formed over the distal adapter 10 and the model of the stump. The thermoplastic on the distal end of the socket is then removed or reshaped until the projections 24a are exposed so that the prosthetic attachment lock 20 and the prosthetic limb 50 can be attached. When making a fiber reinforced laminated socket, the reinforcing fiber is positioned across the sides of the socket and across the bottom surface 24 of the distal adaptor 10 between the projections 24a. A flat laminating plate is then attached to the projections 24a, and the laminating resin is formed over the model of the stump and the distal adaptor. The flat laminating plate is then removed, leaving a flat surface for attaching the prosthetic attachment lock 20 and the prosthetic limb 50.

In use, the amputee applies the stump liner to the residual limb stump such that the lock pin 60 is located at the end of the stump. The user then steps into, or pulls on, the socket 40. As the user does so, the end of the lock pin, which may initially bear against the inner surface 42, smoothly moves from engagement with the inner surface 42 of the socket to engagement with the part-spherical top surface 22 of the distal adapter due to the surface radius at 44. The part-spherical surface 22 then guides the lock pin 60 toward the pin bore 26. Eventually, the lock pin fits into, and extends through, the pin bore 26 of the distal adapter and through the pin bore 28 of the lock body 20A. As this occurs, the lock gear 86 rotates to permit the lock pin 60 to pass through the pin bore 28, but the one-way clutch prevents its removal. Simultaneously, an air tight seal is formed between the residual stump and the inner surface 42 of the socket, causing air to be expelled through the air holes 27 and 48, and through the one way valve 32c. The one way valve, moreover, prevents air return so as to assure a suction lock.

The user can then rotate the button 100 so as to rotate the gear 86, thereby further and securely locking the lock pin 60 in the pin bore 28. A slot at the end of the push button will accept a coin or the head of a screwdriver to assist in locking down the lock pin. This presses the body 62 onto the upper surface 22 and compresses the seal material 66 to prevent air leakage past the pin bore 26. It also creates an upward reaction load on the lock pin 60, which is transferred to the one-way clutch.

When it is desired to remove the stump from the prosthesis, the user pushes the button 100 in the direction A. Since the turning load applied onto the gear 86 by the reaction load on the lock pin 60 is resisted by a one-way clutch which is defined between the sleeves 88 and 96, and which is not incorporated into the centering axle 82, the centering axle 82 can readily move independent of this load and can easily slide in response to the pressure on the button 100 to release the lock pin 60.

Obviously, numerous modifications and variations of the present invention are possible in light of the above teachings. For example, the distal adaptor 10 and the prosthetic attachment lock could be combined in a single unit. It is therefore to be understood that the invention may be practiced otherwise than as specifically described herein.

What is claimed is:

1. A prosthetic attachment lock, comprising:

a lock body having a pin bore into which a lock pin may be inserted;

a locking device in said lock body, said locking device being engageable with a lock pin in said lock body to undirectionally lock the lock pin in the lock body while permitting insertion of the lock pin in the lock body; and a one way valve positioned in said lock body.

2. The prosthetic attachment lock of claim 1, further comprising a muffler cooperating with said one way valve.

3. The prosthetic attachment lock of claim 1, further comprising a lock pin and means for providing an airtight seal around the lock pin in the pin bore.

* * * * *